United States Patent
Besner et al.

(12)

(10) Patent No.: US 6,387,878 B1
(45) Date of Patent: *May 14, 2002

(54) METHODS OF TREATING INTESTINAL ISCHEMIA USING HEPARIN-BINDING EPIDERMAL GROWTH FACTOR

(75) Inventors: Gail E. Besner, Dublin; Srikumar B. Pillai, Columbus, both of OH (US)

(73) Assignee: Children's Hospital Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/518,950

(22) Filed: Mar. 6, 2000

Related U.S. Application Data

(63) Continuation of application No. 09/181,974, filed on Sep. 29, 1998, now Pat. No. 6,191,109.
(60) Provisional application No. 60/063,858, filed on Oct. 31, 1997.

(51) Int. Cl.$^7$ .......................... A61K 38/00; A61K 38/18
(52) U.S. Cl. .......................... 514/12; 514/12; 424/551; 435/325; 435/69.1; 530/350; 530/399; 536/23.5
(58) Field of Search .......................... 514/12; 424/551; 435/325, 69.1; 530/350, 399; 536/23.5

(56) References Cited

U.S. PATENT DOCUMENTS

| 5,057,494 A | * | 10/1991 | Sheffield ...................... 514/12 |
| 5,811,393 A | | 9/1998 | Klagsburn et al. ............ 514/12 |
| 6,191,109 B1 | * | 2/2001 | Besner ........................ 514/12 |

FOREIGN PATENT DOCUMENTS

| WO | WO 92/06705 | * | 4/1992 |

OTHER PUBLICATIONS

Barnard et al., "Epidermal Growth Factor–Related Peptides and Their Relevance to Gastrointestinal Pathophysiology," *Gastroenterology*, 108:564–580 (1995).

Bell et al., "The Microbial Flora and Antimicrobial Therapy of Neonatal Peritonitis," *J. Ped. Surg.*, 15:569 (1980).

Besner et al., "Isolation and Characterization of a Macrophage–Derived Heparin–Bbinding Growth Factor," *Cell Regulation*, 1:811–819 (1990).

Besner et al., "Interaction of Heparin–Binding EGF–Like Growth Factor (HB–EGF) with the Epidermal Growth Factor Receptor: Modulation by Heparin, Heparinase, or Synthetic Heparin–Binding HB–EGF Fragments," *Growth Factors*, 7:289–296 (1992).

Carey et al., "Molecular Cloning and Characterization of N–Syndecan, a Novel Transmembrane Heparan Sulfate Proteoglycan," *J. Cell. Biol.*, 117(1):191–201 (1992).

Dignass and Podolsky, "Cytokine Modulation of Intestinal Epithelial Cell Resitution: Cental Role of Transforming Growth Factor β," *Gastroenterology*, 105:1323–1332 (1993).

Higashiyama et al., "A Heparin–Binding Growth Factor Secreted by Macrophage–Like Cells That Is Related to EGF," *Science*, 251:936–939 (1991).

Miyazaki et al., "Oxidative Stress Increases Gene Expression of Heparin–Binding EGF–like Growth Factor and Amphiregulin in Cultured Rat Gastric Epithelial Cells," *Biochem. Biophys. Res. Comm.*, 226:542–546 (1996).

Parks et al., "Contributions of Ischemia and Reperfusion to Mucosal Lesion Formation,"*Am. J. Physiol.*, 250:G749–753 (1986).

Prigent and Lemoine, "The Type 1 (EGFR–Related) Family of Growth Factor Receptors and Their Ligands," *Prog. Growth Factor Res.*, 4:1–24 (1992).

Villa et al., "Epidermal Growth Factor Reduces Ischemia–Reperfusion Injury in Rat Small Intestine," *Gastroenterology*, 110 (4 Suppl.):A372 (1996).

* cited by examiner

*Primary Examiner*—Christopher S. F. Low
*Assistant Examiner*—Chih-Min Kam
(74) *Attorney, Agent, or Firm*—Marshall, Gerstein, & Borun

(57) ABSTRACT

The present invention provides methods of treating pathologic conditions associated with intestinal ischemia. In the methods, patients at risk for or suffering from intestinal ischemia are treated with a heparin-binding epidermal growth factor product.

1 Claim, No Drawings

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 624 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..624

(xi) SEQUENCE DESCRIPTION: SEQ ID NO: 1:

| | | | | | | | | | | | | | | | | |
|---|---|---|---|---|---|---|---|---|---|---|---|---|---|---|---|---|
| ATG | AAG | CTG | CTG | CCG | TCG | GTG | GTG | CTG | AAG | CTC | TTT | CTG | GCT | GCA | GTT | 48 |
| Met | Lys | Leu | Leu | Pro | Ser | Val | Val | Leu | Lys | Leu | Phe | Leu | Ala | Ala | Val | |
| 1 | | | | 5 | | | | | 10 | | | | | 15 | | |
| CTC | TCG | GCA | CTG | GTG | ACT | GGC | GAG | AGC | CTG | GAG | CGG | CTT | CGG | AGA | GGG | 96 |
| Leu | Ser | Ala | Leu | Val | Thr | Gly | Glu | Ser | Leu | Glu | Arg | Leu | Arg | Arg | Gly | |
| | | | 20 | | | | | 25 | | | | | 30 | | | |
| CTA | GCT | GCT | GGA | ACC | AGC | AAC | CCG | GAC | CCT | CCC | ACT | GTA | TCC | ACG | GAC | 144 |
| Leu | Ala | Ala | Gly | Thr | Ser | Asn | Pro | Asp | Pro | Pro | Thr | Val | Ser | Thr | Asp | |
| | | 35 | | | | | 40 | | | | | 45 | | | | |
| CAG | CTG | CTA | CCC | CTA | GGA | GGC | GGC | CGG | GAC | CGG | AAA | GTC | CGT | GAC | TTG | 192 |
| Gln | Leu | Leu | Pro | Leu | Gly | Gly | Gly | Arg | Asp | Arg | Lys | Val | Arg | Asp | Leu | |
| | 50 | | | | | 55 | | | | | 60 | | | | | |
| CAA | GAG | GCA | GAT | CTG | GAC | CTT | TTG | AGA | GTC | ACT | TTA | TCC | TCC | AAG | CCA | 240 |
| Gln | Glu | Ala | Asp | Leu | Asp | Leu | Leu | Arg | Val | Thr | Leu | Ser | Ser | Lys | Pro | |
| 65 | | | | | 70 | | | | | 75 | | | | | 80 | |
| CAA | GCA | CTG | GCC | ACA | CCA | AAC | AAG | GAG | GAG | CAC | GGG | AAA | AGA | AAG | AAG | 288 |
| Gln | Ala | Leu | Ala | Thr | Pro | Asn | Lys | Glu | Glu | His | Gly | Lys | Arg | Lys | Lys | |
| | | | | 85 | | | | | 90 | | | | | 95 | | |
| AAA | GGC | AAG | GGG | CTA | GGG | AAG | AAG | AGG | GAC | CCA | TGT | CTT | CGG | AAA | TAC | 336 |
| Lys | Gly | Lys | Gly | Leu | Gly | Lys | Lys | Arg | Asp | Pro | Cys | Leu | Arg | Lys | Tyr | |
| | | | 100 | | | | | 105 | | | | | 110 | | | |
| AAG | GAC | TTC | TGC | ATC | CAT | GGA | GAA | TGC | AAA | TAT | GTG | AAG | GAG | CTC | CGG | 384 |
| Lys | Asp | Phe | Cys | Ile | His | Gly | Glu | Cys | Lys | Tyr | Val | Lys | Glu | Leu | Arg | |
| | | 115 | | | | | 120 | | | | | 125 | | | | |
| GCT | CCC | TCC | TGC | ATC | TGC | CAC | CCG | GGT | TAC | CAT | GGA | GAG | AGG | TGT | CAT | 432 |
| Ala | Pro | Ser | Cys | Ile | Cys | His | Pro | Gly | Tyr | His | Gly | Glu | Arg | Cys | His | |
| | 130 | | | | | 135 | | | | | 140 | | | | | |
| GGG | CTG | AGC | CTC | CCA | GTG | GAA | AAT | CGC | TTA | TAT | ACC | TAT | GAC | CAC | ACA | 480 |
| Gly | Leu | Ser | Leu | Pro | Val | Glu | Asn | Arg | Leu | Tyr | Thr | Tyr | Asp | His | Thr | |
| 145 | | | | | 150 | | | | | 155 | | | | | 160 | |
| ACC | ATC | CTG | GCC | GTG | GTG | GCT | GTG | GTG | CTG | TCA | TCT | GTC | TGT | CTG | CTG | 528 |
| Thr | Ile | Leu | Ala | Val | Val | Ala | Val | Val | Leu | Ser | Ser | Val | Cys | Leu | Leu | |
| | | | | 165 | | | | | 170 | | | | | 175 | | |
| GTC | ATC | GTG | GGG | CTT | CTC | ATG | TTT | AGG | TAC | CAT | AGG | AGA | GGA | GGT | TAT | 576 |
| Val | Ile | Val | Gly | Leu | Leu | Met | Phe | Arg | Tyr | His | Arg | Arg | Gly | Gly | Tyr | |
| | | | 180 | | | | | 185 | | | | | 190 | | | |
| GAT | GTG | GAA | AAT | GAA | GAG | AAA | GTG | AAG | TTG | GGC | ATG | ACT | AAT | TCC | CAC | 624 |
| Asp | Val | Glu | Asn | Glu | Glu | Lys | Val | Lys | Leu | Gly | Met | Thr | Asn | Ser | His | |
| | 195 | | | | | 200 | | | | | 205 | | | | | |

(2) INFORMATION FOR SEQ ID NO: 2:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO: 2:

| | | | | | | | | | | | | | | | |
|---|---|---|---|---|---|---|---|---|---|---|---|---|---|---|---|
| Met | Lys | Leu | Leu | Pro | Ser | Val | Val | Leu | Lys | Leu | Phe | Leu | Ala | Ala | Val |
| 1 | | | | 5 | | | | | 10 | | | | | 15 | |
| Leu | Ser | Ala | Leu | Val | Thr | Gly | Glu | Ser | Leu | Glu | Arg | Leu | Arg | Arg | Gly |
| | | | 20 | | | | | 25 | | | | | 30 | | |
| Leu | Ala | Ala | Gly | Thr | Ser | Asn | Pro | Asp | Pro | Pro | Thr | Val | Ser | Thr | Asp |
| | | 35 | | | | | 40 | | | | | 45 | | | |
| Gln | Leu | Leu | Pro | Leu | Gly | Gly | Gly | Arg | Asp | Arg | Lys | Val | Arg | Asp | Leu |
| | 50 | | | | | 55 | | | | | 60 | | | | |
| Gln | Glu | Ala | Asp | Leu | Asp | Leu | Leu | Arg | Val | Thr | Leu | Ser | Ser | Lys | Pro |

-continued

```
           65                  70                  75                  80
   Gln Ala Leu Ala Thr Pro Asn Lys Glu Glu His Gly Lys Arg Lys Lys
                       85                  90                  95
   Lys Gly Lys Gly Leu Gly Lys Lys Arg Asp Pro Cys Leu Arg Lys Tyr
                   100                 105                 110
   Lys Asp Phe Cys Ile His Gly Glu Cys Lys Tyr Val Lys Glu Leu Arg
               115                 120                 125
   Ala Pro Ser Cys Ile Cys His Pro Gly Tyr His Gly Glu Arg Cys His
           130                 135                 140
   Gly Leu Ser Leu Pro Val Glu Asn Arg Leu Tyr Thr Tyr Asp His Thr
   145                 150                 155                 160
   Thr Ile Leu Ala Val Val Ala Val Val Leu Ser Ser Val Cys Leu Leu
                   165                 170                 175
   Val Ile Val Gly Leu Leu Met Phe Arg Tyr His Arg Arg Gly Gly Tyr
                   180                 185                 190
   Asp Val Glu Asn Glu Glu Lys Val Lys Leu Gly Met Thr Asn Ser His
               195                 200                 205
```

METHODS OF TREATING INTESTINAL ISCHEMIA USING HEPARIN-BINDING EPIDERMAL GROWTH FACTOR

This application is a continuation of 09/181,974 filed Sep. 29, 1998, now U.S. Pat. No. 6,191,109 which claims the benefit of the filing date of United States provisional application Ser. No. 60/063,858 filed Oct. 31, 1997 now ABN.

FIELD OF THE INVENTION

The present invention generally relates to prevention and/or treatment of ischemia-induced intestinal injury. More particularly the invention relates to prevention and/or treatment of intestinal injury using heparin-binding epidermal growth factor (HB-EGF) products.

BACKGROUND OF THE INVENTION

Hemorrhagic disorders and ischemic states are the two major classes of gastrointestinal circulatory disorders. A sudden reduction in the blood supply to a tissue is considered to be an ischemic event. Intestinal ischemic events continue to play a major role in the morbidity and mortality of numerous patients. Ischemic injury to the small intestine results in mucosal destruction, bacterial translocation, and perforation. Parks et al., *Am. J. Physiol.*, 250: G749–753 (1986) attributes much of the injury associated with ischemic episodes to the reperfusion phenomena that begin when blood flow is restored. Immediately after an ischemic event, the intestinal epithelium undergoes desquamation with destruction of the lamina propria. At a cellular level, ischemia leads to depletion of ATP and loss of cytoskeletal integrity. With return of the blood supply (i.e., reperfusion), there is continued destruction of the villus structures. These injuries manifest themselves in disease states such as necrotizing enterocolitis and can lead to overwhelming sepsis and multisystem organ failure. Recovery from an ischemic event depends on rapid proliferation and migration of intestinal epithelial cells to regenerate damaged villi. Restitution requires the presence of multiple substances, including cytokines, hormones, and growth factors. Dignass and Podolsky, *Gastroenterology*, 105: 1323–1332 (1993) reports that transforming growth factor-α (TGF-α), interleukin-1β (IL-1β), interferon-γ (IFN-γ), and epidermal growth factor (EGF) have been shown to enhance restitution, possibly through increased production of transforming growth factor-β (TGF-β). These substances act to remodel the intestine after injury and to modulate the inflammatory response.

HB-EGF was originally identified in 1990 as a macrophage-secreted heparin binding growth factor. Like other members of the EGF family, HB-EGF exerts its biological effects by binding to the erb class of EGF receptor (EGF-R) molecules. However, unlike most members of the EGP family including EGF, HB-EGF binds heparin with a high affinity. Heparin appears to potentiate binding of HB-EGF to the signal-transducing EGF-R, and may also modulate the biologic effects of the growth factor on target cells, including cellular migration and proliferation. HB-EGF is mitogenic for fibroblasts, smooth muscle cells and epithelial cells, but not for endothelial cells. In addition, HB-EGF is produced by epithelial cells and acts as an autocrine growth factor for these cells. It is a heat-resistant, cationic protein, with a molecular weight of approximately 22,000 kDa that elutes from heparin-affinity chromatography columns with 1.0 M NaCl.

The cloning of a cDNA encoding human HB-EGF (or HB-EHM) is described in Higashiyama et al., *Science*, 251: 936–939 (1991) and in a corresponding international patent application published under the Patent Cooperation Treaty as International Publication No. WO 92/06705 on Apr. 30, 1992. Both publications are hereby incorporated by reference herein. The sequence of the protein coding portion of the cDNA is set out in SEQ ID NO: 1 herein, while the deduced amino acid sequence is set out in SEQ ID NO: 2. Mature HB-EGF is a secreted protein that is processed from a transmembrane precursor molecule (pro-HB-EGF) via extracellular cleavage. The predicted amino acid sequence of the full length HB-EGF precursor represents a 208 amino acid protein. A span of hydrophobic residues following the translation-initiating methionine is consistent with a secretion signal sequence. Two threonine residues ($Thr^{75}$ and $Thr^{85}$ in the precursor protein) are sites for O-glycosylation. Mature HB-EGF consists of at least 86 amino acids (which span residues 63–148 of the precursor molecule), and several microheterogeneous forms of HB-EGF, differing by truncations of 10, 11, 14 and 19 amino acids at the N-terminus have been identified. HB-EGF contains a C-terminal EGF-like domain (amino acid residues 30 to 86 of the mature protein) in which the six cysteine residues characteristic of the EGF family members are conserved and which is probably involved in receptor binding. HB-EGF has an N-terminal extension (amino acid residues 1 to 29 of the mature protein) containing a highly hydrophilic stretch of amino acids to which much of its ability to bind heparin is attributed. Besner et al., *Growth Factors*, 7: 289–296 (1992), which is hereby incorporated by reference herein, identifies residues 20 to 25 and 36 to 41 of the mature HB-EGF protein as involved in binding cell surface heparin sulfate and indicates that such binding mediates interaction of HB-EGF with the EGF receptor.

The EGF family comprises at least five polypeptides: EGF, HB-EGF, TGF-α, amphiregulin (AR), and betacellulin. For reviews of the family, see Barnard et al., *Gastroenterology*, 108: 564–580 (1995) and Prigent and Lemoine, *Prog. Growth Factor Res.*, 4: 1–24 (1992). The amino acid sequence homology of HB-EGF to the EGF family members is 40 (compared to EGF) to 53% (compared to AR) between the first and sixth cysteine residues in the EGF-like domains, but HB-EGF exhibits lower homology when the full length sequences are compared. Overall, HB-EGF most closely resembles AR in that the two polypeptides exhibit the highest homology, appear to have a similar number of amino acids, and include the N-terminal extension of highly hydrophilic amino acids upstream of the EGF-like domain.

Administration of EGF to prevent tissue damage after an ischemic event in the brains of gerbils has been reported in U.S. Pat. No. 5,057,494 issued Oct. 15, 1991 to Sheffield. The patent projects that EGF "analogs" having greater than 50% homology to EGF may also be useful in preventing tissue damage and that treatment of damage in myocardial tissue, renal tissue, spleen tissue, intestinal tissue, and lung tissue with EGF or EGF analogs may be indicated. However, the patent includes no experimental data supporting such projections.

The small intestine receives the majority of its blood supply from the SMA, but also has a rich collateral network such that only extensive perturbations of blood flow lead to pathologic states. Villa et al., *Gastroenterology*, 110(4 Suppl): A372 (1996) reports that in a rat model of intestinal ischemia in which thirty minutes of ischemia are caused by occlusion of the superior mesenteric artery (SMA), pretreatment of the intestines with EGF attenuated the increase in intestinal permeability compared to that in untreated rats. The intestinal permeability increase is an early event in intestinal tissue changes during ischemia. Multiple animal models, like that described in Villa et al., supra have been used to study the effects of ischemic injury to the small bowel. Since the small intestine has such a rich vascular supply, researchers have used complete SMA occlusion to study ischemic injury of the bowel. Animals who experience total SMA occlusion suffer from extreme fluid loss and uniformly die from hypovolemia and sepsis, making models of this type useless for evaluating the recovery from intestinal ischemia. Nevertheless, the sequence of morphologic and physiologic changes in the intestines resulting from ischemic injury has remained an area of intense examination.

Miyazaki et al., *Biochem Biophys Res Comm*, 226: 542–546 (1996) discusses the increased expression in a rat gastric mucosal cell fine of HB-EGF and AR resulting from oxidative stress. The authors speculate that the two growth factors may trigger the series of reparative events following acute injury (apparently ulceration) of the gastrointestinal tract. To date, there has been no published report of administration of HB-EGF in vivo for any purpose, much less to test its ability to protect the gastrointestinal tract from injury from an ischemic event.

The prevention and treatment of ischemic damage in the clinical setting therefore continues to be a challenge in medicine. There thus exists a need in the art for models for testing the effects of potential modulators of ischemic events and for methods of preventing and/or treating ischemic damage, particularly ischemic damage to the intestines.

SUMMARY OF THE INVENTION

In a first aspect, the invention provides methods of treating pathological conditions associated with intestinal ischemia by administering an HB-EGF product to patients.

As used herein, "BB-EGF product" includes HB-EGF proteins comprising about amino acid 63 to about amino acid 148 of SEQ ID NO: 2; HB-EGP proteins comprising about amino acid 73 to about amino acid 148 of SEQ ID NO: 2; HB-EGF proteins comprising about amino acid 74 to about amino acid 148 of SEQ ID NO: 2; HB-EGF proteins comprising about amino acid 77 to about amino acid 148 of SEQ ID NO: 2; HB-EGF proteins comprising about amino acid 82 to about amino acid 148 of SEQ ID NO: 2; HB-EGF proteins comprising a continuous series of amino acids of SEQ ID NO: 2 which exhibit less than 50% homology to EGF and which are efficacious in the rat model specified below; fusion proteins comprising the foregoing HB-EGF proteins; and the foregoing HB-EGF proteins including conservative amino acid substitutions. Conservative amino acid substitions are understood by those skilled in the art. The HB-EGF products may be isolated from natural sources known in the art [e.g., the U-937 cell line (ATCC CRL 1593)], chemically synthesized, or produced by recombinant techniques such as disclosed in WO92/06705, supra, the disclosure of which is hereby incorporated by reference. In order to obtain HB-EGF products of the invention, HB-EGF precursor proteins may be proteolytically processed in situ. The HB-EGF products may be post-translationally modified depending on the cell chosen as a source for the products.

The administration of HB-EGF products is preferably accomplished with a pharmaceutical composition comprising an HB-EGF product and a pharmaceutically acceptable carrier. The carrier may be in a wide variety of forms depending on the route of administration. The route of administration may be oral, rectal, parenteral, or through a nasogastric tube. Examples of parenteral routes of administration are intravenous, intraperitoneal, intramuscular, or subcutaneous injection. The presently preferred route of administration is the oral route as the present invention contemplates that the acid stability of HB-EGF is a unique factor as compared to, for example, EGF. The HB-EGF pharmaceutical composition may also include other ingrediants to aid solubility, or for buffering or preservation purposes. Pharmaceutical composition containing HB-EGF products comprises HB-EGF at a concentration of about 0.5 to 10 mg/ml and preferably at a concentration of 1 mg/ml in saline. Addition of other bioactive compounds [e.g., antibiotics, free radical scavenging or conversion materials (e.g., vitamin E, beta-carotene, BHT, ascorbic acid, and superoxide dimutase), fibrolynic agents (e.g., plasminogen activators), and slow-release polymers] to the HB-EGF compounds or separate administration of the other bioactive compounds is also contemplated.

As used herein, "pathological conditions associated with intestinal ischemia" includes conditions which directly or indirectly cause intestinal ischemia (e.g., premature birth; birth asphyxia; congenital heart disease; cardiac disease; polycythemia; hypoxia; exchange transfusions; low-flow states; atherosclerosis, embolisms or arterial spasms; ischemia resulting from vessel occlusions in other segments of the bowel; ischemic colitis; and intestinal torsion such as occurs in infants and particularly in animals) and conditions which are directly or indirectly caused by intestinal ischemia (e.g., necrotizing enterocolitis, shock, sepsis, and intestinal angina). Thus, the present invention contemplates administration of HB-EGF products to patients in need of such treatment including patients at risk for intestinal ischemia, patients suffering from intestinal ischemia, and patients recovering from intestinal ischemia. The administration of HB-EGF to patients is contemplated in both the pediatric and adult populations.

More particularly, the invention contemplates a method of reducing necrosis associated with intestinal ischemia comprising administering an HB-EGF product to a patient at risk for, suffering from, or recovering from intestinal ischemia. Also contemplated is a method of protecting intestinal epithelial cells from hypoxia comprising exposing the cells to an HB-EGF product. Administration of, or exposure to, HB-EGF products reduces lactate dehyrogenase efflux from intestinal epithelial cells, maintains F-actin structure in intestinal epithelial cells, increases ATP levels in intestinal epithelial cells, and induces proliferation of intestinal epithelial cells.

In view of the efficacy of HB-EGF in protecting intestinal tissue from ischemic events, it is contemplated that HB-EGF has a similar protective effect on myocardial, renal, spleen, lung, and liver tissue.

In another aspect, the invention provides a novel animal model of intestinal ischemia, designated herein a model of "segmental" intestinal ischemia, that is useful for evaluating the efficacy of putative therapeutics. Mammals, preferably rats, are subjected to reversible arterial occlusion, wherein a first order branch of the SMA and terminal collateral branches are occluded. Preferably, the first order branch of the SMA is selected from the group consisting of the middle ileum and the distal ilieum. Also preferably, six to seven terminal collateral branches are occluded. Reversible occlusion may be accomplished by means such as a microvascular clip or sutures.

DETAILED DESCRIPTION OF THE INVENTION

Practice of the methods of the present invention is illustrated in the following examples wherein Example 1 describes production of HB-EGF by recombinant techniques and demonstrations of activity of the recombinant protein in various assays including cytoprotection of intestinal epithelial cells from hypoxia in vitro; Example 2 discloses a segmental model of intestinal ischemia in the rat; Example 3 describes the efficacy of HB-EGP in treating intestinal ischemia in the rat model; and Example 4 details treatment of human adults and infants with pathological conditions associated with intestinal ischemia with HB-EGF.

EXAMPLE 1

The effects of treatment of rat intestinal epithelial cells with recombinant human HB-EGF were examined. Specifically, HB-EGF was tested for the ability to induce proliferation of intestinal endothelial cells and also for the ability to protect intestinal epithelial cells from hypoxia. Experiments were also performed to examine the mechanism of HB-EGF cytoprotection. The rat intestinal epithelial cells IEC-18 (ATCC CRL 1589) were used in the experiments.

A. Production of recombinant human HB-EGF (rHB-EGF)

The maltose-binding protein (MBP) fusion system (New England Biolabs, Beverly, Mass.) was used to produce recombinant human HB-EGF. HB-EGF cDNA corresponding to nucleotides 220 to 444 of SEQ ID NO: 1 (encoding amino acids 74–148 of the 208-amino acid HB-EGF precursor molecule) was cloned into plasmid pMAL-c2 at the Xmnl and HindIII sites. $E.\ coli$ strain BL21 (F ompT $r_B^- m_S^-$) (Novagen, Madison, Wis.) containing this construct was grown at 37° C. in LB broth (Gibco/BRL, Gaithersburg, Md.) containing 2 g/L glucose (Gibco/BRL) and 100 μg/ml ampicillin (Sigma, St. Louis, Mo.) to an $OD_{600}$ of 0.2–0.3. To induce expression, IPTG (Promega, Madison, Wis.) was added to a final concentration of 0.3 mM. After a 3 hour incubation at 37° C., cells were harvested by centrifugation (4,000×g, 20 minutes) and the cell pellet was resuspended in MBP buffer (10 mM Tris-Ci, 200 mM NaCl, 1 mM EDTA) containing 1 mM PMSF (Sigma) and frozen overnight at 20° C. Thawed cell sample was lysed with a french press (14,000 psi) and the insoluble fraction was removed by centrifugation (9,000×g, 30 minutes). The supernatant was passed over an amylose resin column (New England Biolabs) and fusion protein was eluted in MBP buffer containing 10 mM maltose (Sigma). rHB-EGF was cleaved from MBP with Factor Xa (0.5%, w/w) (Boehringer Mannheim, Indianapolis, Ind.) at 23° C. for 16 hours. Cleaved products were applied to a TSK-heparin 5PW column (8×75 mm, TosoHaas, Philadelphia, Pa.) that was equilibrated with buffer (10 mM Tris-HCI pH 7.4, 0.2M NaCl). The column was washed with equilibration buffer and bound proteins were eluted with a 40 ml linear grdient of 0.2–2.0M NaCl in 10 mM Tris-HCI pH 7.4 at 1 ml/min using an FPLC system (Pharmacia LKB Biotechnology, Piscataway, N.J.). One milliliter fractions are collected and assayed in an EGF radioreceptor assay essentially as described in Besner et al. (1992), supra. Fractions showing peak displacement of $^{125}$I-EGF binding were pooled, adjusted to contain 5% acetonitrile and 0.1% trifluoroacetic acid and subjected to reverse phase HPLC (RP-HPLC). RP-HPLC was performed in a Hitachi (San Hose, Calif.) HPLC system using a Vydac $C_4$ column (0.46×25 cm, 5 μm particle size; The Separations Group, Hesperia, Calif.) that was equilibrated with water containing 5% acetonitrile and 0.1% trifluoroacetic acid. The HB-EGF sample was injected onto the column and the column was eluted using a multilinear gradient of 5% acetonitrile (isocratic) for 5 minutes, 5–15% acetonitrile over 5 minutes, 15–40% over 120 minutes, 40–90% over 1 minute, 90% isocratic for 10 minutes, 90–5% over 1 minute, and 5% isocratic for 33 minutes. The flow rate was 1 ml/min throughout and 1 ml fractions were collected. After these purification steps, the absorbance peak eluting at 19% acetonitrile is shown by SDS-PAGE to be a single band migrating at approximately 13 kDA. $NH_2$-terminal amino acid sequencing of the pure protein produced in this fashion confirms the sequence for HB-EGF. The rHB-EGF was biologically active in the EGF-radioreceptor assay and a Balb/c 3T3 DNA synthesis assay [essentially as described in Besner et al., *Cell Regulation*, 1: 811–819 (1990)].

B. Recombinant HB-EGF is mitogenic for intestinal epithelial cells

IEC-18 cells were cultured in Dulbecco's Modified Eagle Medium (DMEM) containing 5% fetal bovine serum (FBS), 50 μg/ml penicillin and 50 units/ml streptomycin in a humidified atmosphere of 10% $CO_2$ at 37° C. Cells were then seeded at a density of $1×10_5$ cells/well in a 24 well plate (2 ml/well). After a 24 hour incubation, medium was changed to DMEM/1% FBS (2 ml/well) and cells were allowed to incubate for an additional 24 hours. Cells in four of the wells were trypsinized and counted at Day 0 using a Coulter Counter®. rHB-EGF was added to duplicate wells on Day 0 at a concentration of 100 ng/ml. This concentration of rHB-EGF was determined as optimal from preliminary dose-response curves for rHB-EGF-stimulated proliferation of IEC-18 cells. Cells in duplicate wells were trypsinized and counted on days 1 through 5.

Under normoxic conditions, rHB-EGF-treated cells had 1.85 fold greater increase in number compared to non-treated cells by day 4 ($p<0.05$). Further, the mitogenic response of IEC-18 cells to rHB-EGF was dose-dependent, with maximal stimulation by 100 ng/ml.

C. Recombinant HB-EGF to protects intestinal epithelial cells against hypoxia

Lactate dehyrogenase (LDH) efflux was used as a measure of cell injury after hypoxia. IEC-18 cells were seeded at a density of $5×10^4$ cells/well in DMEM/5% FBS in 24 well plates (2 ml/well). After 24 hours, medium was changed to DMEM/1% FBS (2 ml/well). This plating density resulted in approximately 75% confluency. After an additional 24 hour incubation period, the medium was replaced with Kreb's buffer (116 mM NaCl, 1.0 mM $NaH_2PO_4$, 25.0 mM $NaHCO_3$, 5.4 mM KCl, 1.8 mM $CaCl_2$, and 0.8 mM $MgSO_4$) and the cells were placed in an anaerobic incubator with $FiO_2 \leq 1\%$. Aliquots (50 μl) of media were removed at specific time intervals and were assayed for LDH efflux using a Cytox 96 assay. At the end of the experiment, cells were lysed with PBS/0.1% Triton-100 and total LDH content was determined. LDH efflux was expressed as the percentage of total LDH activity. Based on preliminary experiments which demonstrated approximately 20–25% cell death after 10 hours of hypoxia and 100% cell death after 14 hours of hypoxia, a 10 hour anaerobic period was used in the subsequent studies.

To test the growth factor effects, 100 ng/ml rHB-EGF was added to some wells 12 hours prior to the initiation of hypoxia. After 10 hours of hypoxia, plates were removed from the anaerobic chamber, medium changed to DMEM/5% FBS, and cells were allowed to recover for 48 hours. During recovery, some wells received additional (post-hypoxia) rHB-EGF (100 ng/ml) treatment. Aliquots (50 μl) of media were removed from the wells at 0, 12, 24, 36, and 48 hours of recovery and LDH efflux was measured.

Intestinal cells that received rHB-EGF either pre-hypoxia or both pre- and post-hypoxia showed a significantly lower LDH release during recovery from hypoxia compared to non-treated cells. Although there was very little LDH efflux immediately after hypoxia, by 48 hours, non-treated cells had an LDH release of 22.8% compared to 7.48% for cells that had been pre-treated with HB-EGF (p<0.009) or to 9.1% for cells that had been both pre-treated and post-treated with HB-EGF (P<0.009). Cells that received HB-EGF during only the post-hypoxic period did not have a significantly lower LDH release compared to cells that were not treated with HB-EGF.

D. Effects of rHB-EGF on cytoskeletal structure, ATP stores, and post-hypoxia proliferation To examine IEC-18 cytoskeletal structure, IEC-18 cells were seeded at $5\times10^3$ cells/well in DMEM/5% FBS (500 $\mu$l/chamber) in 8-well chamber slides. Cells were incubated for 24 hours after which the medium was changed to DMEM/1% FBS. rHB-EGF (100 ng/ml) was then added to specific wells. After an additional 12 hours, medium was changed to Kreb's buffer and cells were placed in the anaerobic chamber for 10 hours. Following this, medium was changed to DMEM/5% FBS and cells were incubated for an additional 24 or 48 hours. Medium was aspirated from the chambers, cells were fixed for thirty minutes in 10% formalin (buffered with PBS), and slides were washed twice in PBS. Cells were simultaneously stained with rhodamine phalloidin to detect filamentous (F) actin and Dnase I fluorescein to detect globular (G) actin. Confocal analysis of the cells was performed with the Zeiss LSM inverted microscope using a krypton/argon mixed gas laser and a Zeiss filter set, utilizing emissions filters of 568 and 488. Images were digitally recorded.

Under normal circumstances, monomeric G-actin is polymerized to produce F-actin in an AT-dependent manner. F-actin staining of cells is present in the cortical region (peripheral) in cells having an intact cytoskeleton, whereas G-actin accumulation is indicative of cytoskeletal injury. Immediately after anaerobic exposure, the respective proportions of F-actin and G-actin were similar between rHB-EGF-treated and non-treated cells. However, after 24 hours of recovery, IEC-18 cells that received rHB-EGF prior to anaerobic exposure maintained the cortical F-actin cytoskeletal structure compared to non-treated cells which had increase levels of peri-nuclear G-actin staining. By 48 hours, rHB-EGF-treated cells still maintained their F-actin structure, whereas non-treated cells contained predominately G-actin with very little F-actin.

To examine ATP stores in IEC-18 cells, the cells were seeded at a density of $1\times10^5$ cells/well in DMEM/5% FBS in 6 well palates (1 ml/well). Cells were incubated for 24 hours after which the medium was changed to DMEM/1% FBS. rHB-EGF (100 ng/ml) was then added to specific wells. After an additional 12 hours, medium was changed to Kreb's buffer and cells were placed in the anaerobic chamber for 10 hours. Cells were lysed with PBS/0.1% Triton-100 at 0, 24 and 48 hours of recovery. ATP content was measured using an ATP determination kit (Molecular Probes, Eugene, Oreg.). This assay allows quantification of ATP through a luciferin/luciferase-ATP reaction. Bioluminescence was measured with a luminometer (Model LB9501). Initial experiments demonstrated a linear relationship ($r^2=0.960$) between ATP (pmoles) and luminescence. A Bio-Rad $D_c$ protein assay was used to determine total protein content in the samples. Optical density (OD) was measured with a microplate reader (Model EL312). Preliminary standard curves demonstrated a linear relationship ($r^2=0.988$) between protein (mg/ml) and OD.

Both non-treated and rHB-EGF treated cells had ATP levels in the 11–12 nmole/mg range under normoxic conditions. rHB-EGF-treated and non-treated cells had similar decreases in ATP levels in the immediate post-hypoxic period (45% drop vs 50% drop, respectively). However, during the later recovery periods (24 and 48 hours), the HB-EGF-treated cells exhibited a rise in their ATP levels (6.1 nmole/mg), whereas the non-treated cells continued to have decreased ATP content (4.5 nmole/mg).

Post-hypoxia IEC-18 cell proliferation was assessed with a CytoQuant fluorescence assay (Molecular Probes, Eugene, Oreg.). Preliminary experiments demonstrated a linear relationship ($r^2=0.978$) between cell number and fluorescence. IEC-18 cells were seeded at $5\times10^3$ cells/well in DMEM/5% FBS in 96-well plates (200 $\mu$l/well). After 24 hours of incubation, medium was changed to DMEM/1% FBS (200 $\mu$l/well). Some wells received HB-EGF (100 ng/ml) and the cells were incubated for an additional 12 hours. Medium was then changed to Kreb's buffer and the plate was placed in the anaerobic chamber for 10 hours. At 0, 12, 36, and 72 hours of recovery, media was removed and plates were frozen at $-70°$ C. for thirty minutes. The Cytoquant fluoroprobe was added after incubating plate at room temperature for five minutes. Fluorescence was measured in a Cytofluor fluorescent plate reader (Millipore, Bedford, Mass.).

Cytofluorometric measurement of post-hypoxia cellular proliferation of IEC-18 cells showed that cells treated with HB-EGF had a 1.23 fold increase in a cell number compared to non-treated cells by 72 hours of recovery from hypoxia (p<0.05).

The experimental results described above relating to the mitogenic and cytoprotective effects of HB-EGF were orally disclosed at the Columbus Surgical Society Presidential Symposium on Jan. 18, 1997 and at the Annual West Virginia University Resident's Forum on Mar. 7, 1997. The experimental results described above relating to LDH release were disclosed orally and in abstract form at the Childrens' Hospital Research Foundation Research Forum in Columbus, Ohio on Jun. 5, 1997.

HB-EGF was also demonstrated to preserve cytoskeletal structure and increase cellular ATP levels in renal tubular epithelial cells subject to hypoxia. The same cells also released a lower level of LDH during recovery than untreated cells.

The results of the in vitro experiments indicate that in addition to being a mitogen for intestinal epithelial cells, HB-EGF is also a cytoprotective growth factor for these cells during recovery from hypoxia. The in vitro cytoprotective effects of rHB-EGF can be explained, at least in part, by increased cellular ATP levels in rHB-EGF-treated cells with resultant preservation of cytoskeletal structure. An additional beneficial effect of this growth factor is that after the ischemic event, HB-EGF-treated cells have a higher proliferative rate than non-treated cells. The cytoprotective effects of HB-EGF may be enhanced by its ability to bind to heparan sulfate proteoglycans expressed on the surface of intestinal cells. See Carey et al., *J. Cell Biology*, 117(1): 191–201 (1992) for a discussion of heparan sulfate proteoglycans.

EXAMPLE 2

While HB-EGF protected intestinal epithelial cells from hypoxia in vitro, there was no model described in the literature that was useful for examining the effect of HB-EGF on recovery from intestinal ischemia in vio. To determine whether HB-EGF was efficacious in protecting the intestines from the deleterious effects of ischemia in vivo, a novel animal model of segmental intestinal ischemia was developed. The model provides the opportunity to study ischemia-reperfusion injuries in localized segments of bowel without the morbidity and mortality associated with total SMA occlusion in prior animal models. By occluding a first order branch of the superior mesenteric artery (SMA) and by selectively ligating terminal collateral branches, reproducible segmental intestinal ischemia was achieved. Bowel damage ranged from alterations in the villus structure to frank hemorrhagic necrosis of the intestinal wall.

The operative procedure was performed as follows. A total of eighteen rats (age 7 to 9 weeks, 200–265 g) were induced with an intraperitoneal injection of Ketamine-HCl (10 mg/kg) and Xylazine (3 mg/kg). Intravenous access and/or fluid resuscitation were not necessary during the procedure. The abdomen was shaved and painted with betadine. The animal was placed supine on a warming pad set at 40° C., and positioned under an operating microscope. A midline skin incision was made, the linea alba was opened, and the peritoneal cavity was entered. The small intestine, cecum and proximal ascending colon were delivered into the operative field and the superior mesenteric vein was identified. The SMA was located postero-lateral to the vein and was exposed by carefully dissecting apart the mesentery with 0.5 mm micro-surgical forceps. Exposure of this artery and the subsequent steps were performed using an operating microscope. Once the SMA was exposed, the first order branches were evaluated for possible sites of occlusion. Since the mesenteric arcades are longer in the ileal segments, the middle and distal ileum were used as target segments for arterial occlusion. Once a segment was identified, a micro-vascular atraumatic clip (2.0 mm) was placed on the first order mesenteric branch feeding this segment. After the clip was placed, the terminal arterial and venous arcade branches, both proximal and distal to the occluded arcade, were ligated with 5.0 silk sutures. To create a 5 cm segment of ischemic bowel, six to seven terminal branches need to be ligated. Arterial occlusion was maintained for 1 hour. A 4×4 gauze pad was placed over the bowel during this time and was frequently moistened with warm saline. Prior to removing the micro-clip, 0.1% Evan's blue solution (1.5 cc) was injected into the renal vein with a 28 gauge needle to confirm non-perfusion of the ischemic segment. The micro-clip was then removed and Evan's blue, at the same concentration, was injected into the contralateral renal vein to establish return of flow to the ischemic segment. The silk ligatures were left on the terminal branches. The abdomen was closed in a standard fashion. Animals were then placed in a warm incubator (40° C.) until awake (approximately 20 minutes) and were then transferred to individual cages. They received water, but not food, during the post-operative period. Animals were euthanized with $CO_2$ and segments of intestine were removed for histologic analysis at 6 hours after surgery in 6 animals and at 48 hours after surgery in 12 animals.

All eighteen animals survived the operation. Gross changes of the bowel during the arterial occlusion were noted to occur in stages. After 10–15 minutes of ischemia the serosa loses its sheen, and after 15–20 minutes the bowel wall becomes edematous. After 25–35 minutes the bowel color changes from pink to white and later develops a more dusky appearance. The proximal and distal ends of the segment, where the terminal arteries and veins were ligated, have a more bluish appearance, and the smaller veins become dilated. Peristalsis of the affected segment ceases within the first 25 minutes of ischemia. As ischemic time increases, the bowel wall becomes increasingly edematous. Confirmation of ischemia was shown with Evan's blue dye injection, with the dye taken up by the normally perfused bowel, but not by the ischemic segment. Upon termination of arterial occlusion, uptake of the blue dye throughout the previously ischemic bowel confirmed resumption of flow to this area.

After euthanization, the abdomen was re-explored and the segment of ischemic bowel, as well as portions of intestine both proximal and distal to the hypo-perfused segment, were excised and fixed in Histochoice™ for 12 hours. The segments were then cross-sectioned at 1 mm intervals, processed in a standard fashion, and embedded in paraffin. Sections were H&E stained and examined using a standard light microscope. All six animals that were sacrificed at the 6 hour time point showed minor intestinal villus structural change. Instead of the normal elongated distal tip, the villi had more flattened tips with reduction of cytoplasmic content and absence of the brush border. Of twelve animals sacrificed after 48 hours, all showed evidence of villus tip necrosis, and five also developed areas of hemorrhagic transmural necrosis with extensive polymorphonuclear leukocyte infiltration.

Animal care and experimentation described above conformed to standards listed in the National Institute of Health's *Guide for the Care and Use of laboratory Animals*. The experimental protocol was evaluated and approved by the Institutional Animal Care and Use Committee of Children's Hospital (protocol # 01496AR). Each procedure was performed by a single operator without the need for additional assistance. All procedures were performed using sterile technique. The duration of the procedure was 1¼–1½ hours, depending on the difficulty of the dissection.

In comparison to ischemia-reperfusion injury models involving total SMA occlusion the mortality rate of which approaches 100%, the segmental model described herein had a 0% postoperative mortality in the first 48 hours. The development of the segmental model thus allowed the investigation of the effects of potential therapeutic agents during the recovery period.

EXAMPLE 3

The effect of HB-EGF on intestinal ischemia in vivo was then examined using the segmental model.

A total of twelve rHB-EGF-treated and twelve control male Sprague-Dawley rats (220–310 g) were studied. Segmental intestinal ischemia involving a 4.5–5.0 cm length of distal ileum was produced as described in Example 2. Arterial occlusion was maintained for 1 hour. Fifteen minutes prior to removing the microvascular clip, Evan's blue solution was injected intravenously to confirm segmental intestinal S ischemia. Experimental animals then received HB-EGF (20 µg/ml) which was injected intraluminally into the duodenum in a volume of 5 ml of phosphate buffered saline (PBS), which led to filling of the entire gastrointestinal tract from the duodenum to the cecum. Control animals received an injection of 5 ml of PBS only. At the end of the 1 hour ischemic interval, the microvascular clamp was removed and the Evan's blue solution was reinjected intravenously to confirm segmental intestinal reperfusion. Animals received water but no food postoperatively. After 48 hours animals were sacrificed and necropsy performed. The ischemic intestinal segment as well as the bowel just proximal and distal to the ischemic segment were excised. Tissues were placed in Histochoice fixative for 12 hours, cross-sectioned at random intervals and embedded in paraffin. Sections were H & E stained and examined using a standard light microscope. For each animal in the experiment, 4–10 random sections of the ischemic bowel segment were examined for histologic injury. Results are presented in Table 1 below.

TABLE 1

|  | # animals | # sections examined | Tip necrosis | Transmural necrosis | Total injury |
|---|---|---|---|---|---|
| Non-treated | 12 | 92 | 51/92 (55%) | 21/92 (23%) | 72/92 (78%) |
| rHB-EGF-treated | 12 | 94 | 12/94 (13%) | 0/94 (0%) | 12/94 (13%) |

$P < 0.05$

Of the non-treated animals, 55% of the representative sections studied had villous tip necrosis, and 23% of the sections had transmural necrosis. In contrast, in the HB-EGF-treated animals, only 13% of the sections studied had villous tip necrosis, and none of the sections displayed transmural necrosis. Thus, intraluminal HB-EGF administration, in this case delivered 45 minutes after the initiation of the ischemic event, protects the intestine from ischemic injury.

EXAMPLE 4

The following section exemplifies administration of HB-EGF to pediatric patients and adult patients. Administration of HB-EGF is indicated in patients at risk for or suffering from any pathological condition associated with ischemic injury.

A. Administration to pediatric patients

Intestinal injury related to an ischemic event is a major risk factor for neonatal development of necrotizing enterocolitis (NEC). NEC accounts for approximately 15% of all deaths occurring after one week of life in small premature infants. Although most babies who develop NEC are born prematurely, approximately 10% of babies with NEC are full-term infants. Babies with NEC often suffer severe consequences of the disease ranging from loss of a portion of the intestinal tract to the entire intestinal tract. At present, there are no known therapies to decrease the incidence of NEC in neonates.

Babies considered to be at risk for NEC are those who are premature (less than 36 weeks gestation) or those who are full-term but exhibit, e.g., prenatal asphyxia, shock, sepsis, or congenital heart disease. The presence and severity of NEC is graded using the staging system of Bell et al., *J. Ped. Surg.*, 15:569 (1980) as follows:

| Stage I (Suspected NEC) | Any one or more historical factors producing perinatal stress Systemic manifestations - temperature instability, lethargy, apnea, bradycardia Gastrointestinal manifestations -poor feeding, increased pregavage residuals, emesis (may be bilious or test positive for occult blood), mild abdominal distension, occult blood in stool (no fissure) |
|---|---|
| Stage II (Definite NEC) | Any one or more historical factors Above signs and symptoms plus persistant occult or gross gastrointestinal bleeding, marked abdominal distention Abdominal radiographs showing significant intestinal distention with ileus, small-bowel separation (edema in bowel wall or peritoneal fluid), unchanging or persistent "rigid" bowel loops, pneumatosis intestinalls, portal venous gas |
| Stage III (Advanced NEC) | Any one or more historical factors Above sings and symptoms plus deterioration of vital signs, evidence of septic shock, or marked gastrointestinal hemorrhage Abdominal radiographs showing pneumoperitoneum in addition to findings listed for Stage II |

Babies at risk for or exhibiting HB-EGF are treated as follows. Patients receive a daily liquid suspension of HB-EGF (1 mg/kg in saline). The medications are delivered via a nasogastric tube if one is in place, or orally if there is no nasogastric tube in place.

B. Administration to adult patients

Adults also receive a daily liquid suspension containing HB-EGF (1 mg/kg) to drink or through a nasogastric tube if necessary.

Numerous modifications and variations in the practice of the invention are expected to occur to those skilled in the art upon consideration of the foregoing description. Consequently, the only limitations which should be placed on the invention are those which appear in the following claims.

We claim:

1. A method of treating intestinal cell necrosis associated with intestinal ischemia in a patient in need thereof comprising administering to said patients an effective amount of heparin-binding epidermal growth factor product, effective to reduce intestinal cell necrosis.

* * * * *